United States Patent [19]

Arndt et al.

[11] Patent Number: 5,849,946
[45] Date of Patent: Dec. 15, 1998

[54] METHOD OF OBTAINING WATER-FREE 2-TRIMETHYLAMMONIUMETHYL METHACRYLATE CHLORIDE (TMAC) FROM AN AQUEOUS SOLUTION

[75] Inventors: Peter-Joseph Arndt, Seeheim-Jugenheim; Werner Ude, Darmstadt; Klaus Gottmann, Heppenheim; Thomas Kehr, Muehltal, all of Germany

[73] Assignee: Roehm GmbH Chemische Fabrik, Darmstadt, Germany

[21] Appl. No.: 857,900

[22] Filed: May 16, 1997

[30]   Foreign Application Priority Data

May 17, 1996 [DE] Germany ............... 196 20 036.9

[51] Int. Cl.⁶ .................................................. C07C 69/52
[52] U.S. Cl. ............................................................ 560/222
[58] Field of Search ............................................. 560/222

[56]   References Cited

U.S. PATENT DOCUMENTS 5,525,448  11/1996  Larson .

FOREIGN PATENT DOCUMENTS 2732301  1/1979  Germany .

OTHER PUBLICATIONS

Stickler, M; Angew Markromol. Chem (1984) 123/124 85–117.

*Primary Examiner*—Paul J. Killos
*Attorney, Agent, or Firm*—Oblon, Spivak, McClelland, Maier & Neustadt, P.C.

[57]   ABSTRACT

The invention relates to a method of obtaining water-free 2-trimethylammoniumethyl methacrylate chloride (TMAC) characterized in that an aqueous TMAC solution is subjected to the following operations:

(a) Azeotropic removal using an alkyl (meth)acrylate; and
(b) Filtration of the resulting suspension.

16 Claims, No Drawings

METHOD OF OBTAINING WATER-FREE 2-TRIMETHYLAMMONIUMETHYL METHACRYLATE CHLORIDE (TMAC) FROM AN AQUEOUS SOLUTION

BACKGROUND OF THE INVENTION

1. Field of the Invention

The invention relates to an improved method of obtaining water-free 2-trimethylammoniumethyl methacrylate chloride (TMAC) from an aqueous solution.

2. Discussion of the Background

TMAC is useful as a functional monomer for polymeric coatings of pharmaceutical preparations, where it is used as a comonomer with methyl methacrylate and ethyl acrylate (see, e.g. DE 1,617,751). In such applications, a solution in an organic solvent, preferably methanol, is used for the polymerization.

TMAC may be obtained by quaternization of 2-dimethylaminoethyl methacrylate with methyl chloride in the presence of acetone (JP-A-75-43393 (see C.A. 86:73373j). After addition of water and toluene, the toluene phase is first separated out. Residual toluene is removed under vacuum, leaving an aqueous TMAC solution.

U.S. Pat. No. 4,239,876 describes the production of TMAC by quaternization of dimethylaminoethyl methacrylate with methyl chloride in the presence of acrylamide, in an anhydrous medium. The method advantageously suppresses hydrolytic side reactions which occur with preparations carried out in the presence of water. The melt obtained may be used for manufacturing mixed polymers of acrylamide which are employed as flocculants.

U.S. Pat. No. 4,517,380 describes a method of purifying methacrylamidopropyl trimethylammonium chloride and related compounds (among them TMAC) by means of extraction with dichloromethane. The extraction can remove low molecular weight impurities introduced with the dimethylaminoethyl methacrylate fed to the quaternization. The TMAC product may be employed in the manufacture of flocculants.

DE 2,537,378 describes the production of TMAC for use as a monomer in the manufacture of flocculants. TMAC is produced by quaternization of dimethylaminoethyl methacrylate with methyl chloride in 75% aqueous solution. Benzene is added and then decanted, in a washing step. The TMAC product is subsequently subjected to UV polymerization. A drawback of the method is the use of benzene, which is toxic.

JP-A-77-57050 (C.A. 90:169291) describes the stabilization of an aqueous TMAC solution by addition of a benzophenone, e.g. 2,2'-dihydroxy-4-methoxybenzophenone. JP-A-57049 (see C.A. 90:152828) describes the stabilization of an aqueous TMAC solution with nitroso compounds, e.g. nitroso-N-methylaniline at a concentration of 200 ppm. JP-A-77-62193 (see C.A. 90:151610) describes the stabilization of an aqueous TMAC solution with urea compounds or thio compounds. With the use of the described method, stabilized TMAC remained free of polymers after storage for 1 month, and could be polymerized with the addition of initiators.

Undesirable polymerization during storage of aqueous TMAC solutions can be addressed by adding polymerization-inhibiting stabilizers. However, the problem remains for preparing TMAC in a form which is sufficiently pure and free of water to be used as a comonomer with methyl methacrylate and ethyl acrylate in a subsequent polymerization. As a rule, TMAC will contain polymeric TMAC as a contaminant and undesirable byproduct. This polymeric TMAC evidently originates by self-polymerization following the quaternization reaction, during the removal of the solvent water and during storage of the TMAC in solid form. This impurity is less of a problem if the TMAC is later used to produce flocculants than if the TMAC is used to produce polymeric coatings for pharmaceuticals, because pharmaceutical preparations are subject to stricter quality standards.

Using prior methods which involve preparation in an aqueous solution, it has not been possible to produce TMAC without an undesirable amount of contaminating polymer. After removal of the water, heretofore the TMAC would always contain a certain amount of polymer, which would readily precipitate out and cause production problems when the TMAC was used to produce the above-described pharmaceutical polymers. The addition of stabilizers did not solve the problem. The precipitates are sticky, adhering to surfaces of all kinds, leading, e.g., to plugging of filtration apparatus. The walls of reaction vessels become coated with deposits which are impracticably difficult to remove. The pharmaceutical polymers sought to be produced are rendered cloudy and inconsistent.

The use of stabilizers to reduce the polymerization of TMAC is unsatisfactory in that a large amount of stabilizer is required to achieve an appreciable suppression of polymerization during the removal of the water, and this causes problems in the subsequent polymerization to produce the pharmaceutical polymers.

The underlying problem of the present invention is to devise a method of obtaining TMAC whereby TMAC in an aqueous solution following the quaternization reaction is converted to water-free TMAC, without formation of TMAC polymer (or with substantially reduced formation of TMAC polymer in comparison to the state of the art). Further, according to the method, it is desired that no (or essentially no) TMAC polymerization occur during storage of the solid TMAC product.

SUMMARY OF THE INVENTION

This problem is solved according to the invention by a method of obtaining water-free 2-trimethylammoniumethyl methacrylate chloride (TMAC) comprising subjecting an aqueous TMAC solution to:

(a) Azeotropic removal of water using an alkyl (meth) acrylate; and (b) Filtration of the resulting suspension.

Surprisingly, the inventive method leads to TMAC which is substantially or completely free of polymer. Moreover, no detectable polymer formation occurs during storage. Therefore it is no longer necessary to ship or store TMAC in aqueous solution, and thereby it is no longer necessary to provide means of keeping the solution cool and/or to add large amounts of stabilizers. The TMAC obtained, either in dry form or in a mixture with monomers, may be used directly for copolymerization with methyl methacrylate and ethyl methacrylate, in methanol. The abovementioned technical problems of plugging of filters and coating of reactor walls are substantially remedied.

While not wishing to be bound by any particular theory, it is theorized that the inventive result, non-polymerization of TMAC, is due to the mild process conditions. In instances where a small amount of polymer is still produced, it is probably TMAC/(meth)acrylate polymer, which causes minimal problems in a process of radical polymerization of ethyl acrylate, methyl methacrylate, and TMAC to produce polymeric pharmaceutical coatings. The reason is that the contaminating polymer is soluble (to some extent) in the polymerization mixture.

DETAILED DESCRIPTION OF THE PREFERRED EMBODIMENTS

The present method may begin with any aqueous solution of TMAC, as conventionally known in the art, such as that which is obtained, e.g., from quaternization of 2-dimethylaminoethyl methacrylate with methyl chloride in the presence of water. The TMAC content of the solution may be, e.g., in the range 20–90 wt. %. Particularly if the solution is a commercially marketed TMAC solution, it may contain polymerization inhibitors. The water content of the aqueous solution of TMAC is not particularly limited and for example may be within the range of 10–80 wt. %.

Process step (a), azeotropic removal of water using a $C_{1-6}$ alkyl (meth)acrylate, may be carried out under conventional methods known to those of ordinary skill in the art, for example as follows: The $C_{1-6}$ alkyl (meth)acrylate is added to the aqueous solution of TMAC, in a weight ratio in the range 1–2:1, preferably 1.0–1.6:1 ($C_{1-6}$ alkyl (meth)acrylate: aqueous solution of TMAC). An azeotropic mixture is formed thereby. Preferred $C_{1-6}$ alkyl (meth)acrylates are methyl methacrylate and ethyl acrylate, particularly methyl methacrylate. Advantageously, a polymerization-inhibiting stabilizer, e.g. 4-hydroxy-2,2,6,6-tetramethylpiperidinyloxy (trade name Tempol), is added in small amounts, e.g. 0.01–0.001 wt. %. The water can be removed from the mixture with addition of additional air, using a water separator with heating at reflux at a pressure of c. 200–600 mbar, preferably 200–250 mbar and temperatures of c. 40°–90° C., preferably 40°–70° C. This process may take c. 2–10 hr.

After dewatering the suspension will have a water content of $\leq 5$ wt. %, preferably $\leq 4$ wt. %, more preferably $\leq 3$ wt. %, even more preferably $\leq 1$ wt. % and most preferably $\leq 0.5$ wt. %.

The dewatering step is followed by step (b), filtration of the resulting suspension containing TMAC and the $C_{1-6}$ alkyl (meth)acrylate, to remove the $C_{1-6}$ alkyl (meth)acrylate. There is no particular limitation as to the method used to filter the TMAC from the $C_{1-6}$ alkyl (meth)acrylate, and may be conducted by conventional techniques known to those of ordinary skill in the art. Non-limiting examples of suitable techniques include simple filtration, vacuum filtration, suction filtration and centrifugation followed by decanting. The filter cake may be washed by addition of alkyl (meth)acrylate and re-filtration. This may serve as well to remove low molecular weight impurities which may be present, along with stabilizer (if a stabilizer has been used).

The essential feature is the use of a $C_{1-6}$ alkyl (meth) acrylate, e.g. methyl methacrylate. The TMAC obtained has an alkyl (meth)acrylate content of, e.g., 20–50 wt. %, and is substantially or completely free of TMAC polymer. The amount of TMAC polymer present in the TMAC is preferably $\leq 1$ wt. %, more preferably $\leq 0.5$ wt. %, even more preferably $\leq 0.1$ wt. %. A test for the presence of TMAC polymer is to add ethyl acrylate and methyl methacrylate to a methanolic solution of the product; if the mixture remains clear, the product is essentially polymer-free. The TMAC monomer may be directly dissolved in methanol for further processing, or may be dried and stored.

If it is elected to dry the TMAC, preferably mild conditions are used. The temperature, in particular, should be kept low, e.g. not exceeding 50° C. Preferably, lower temperatures are used, e.g. c. 30° C. The duration of the drying process is, e.g., 1–8 hr.

The solid TMAC obtained has very little or no polymer content, by the abovedescribed turbidity test, even after prolonged storage. The solid material can be dissolved in methanol and used to produce pharmaceutical coatings. Difficulties with soiling of apparatus, formation of deposits on reactors, and clouding of the polymer product, are not experienced to any appreciable degree.

Having generally described this invention, a further understanding can be obtained by reference to certain specific examples which are provided herein for purposes of illustration only and are not intended to be limiting unless otherwise specified.

EXAMPLE 94.3 kg methyl methacrylate and 20 g 4-hydroxy-2,2,6,6-tetramethylpiperidinyloxy (Tempol) were charged to a 360 L reaction vessel having a 4 m column of V4A steel with diameter 20 cm, filled with Raschig rings (20×20 mm). 66 kg of a 75% aqueous solution of TMAC, stabilized with c. 600 ppm hydroquinone monomethyl ether, was added.

Dewatering was carried out over c. 4 hr, at c. 230 mbar with a feed of air at 100 L/hr, by heating at reflux over a water separator. The reboiler temperature was 52°–62° C. and the overhead temperature was 48°–52° C.

The resulting suspension containing TMAC and methyl methacrylate was filtered in a pressure filter, e.g. a "filter dryer", at c. 30° C., and washed with a total of 66 kg methyl methacrylate. Then the product was dried c. 4 hr at 50 mbar and c. 30° C. A sample of the dried material was taken, for testing for polymer content and storage stability.

The test for polymer content consisted of dissolving 2.5 g of the solid in 2.5 g methanol, followed by addition of 7 g ethyl acrylate and 13 g methyl methacrylate. The resulting solution was clear, indicating no appreciable polymer content. (If TMAC polymer had been present the solution would have become cloudy.)

The test for storage stability consisted of storing an aliquot of the solid 7 days at 50° C. in a drying cabinet, followed by the test for polymer content as described above. Again the test solution did not become cloudy.

Obviously, numerous modifications and variations of the present invention are possible in light of the above teachings. It is therefore to be understood that within the scope of the appended claims, the invention may be practiced otherwise than as specifically described herein.

This application is based on German Patent Application DE-196,20,036.9 filed with the German Patent Office on May 17, 1996. The entire contents of which are hereby incorporated by reference.

What is claimed as new and desired to be secured by Letters Patent of the United States is:

1. A method of obtaining water-free 2-trimethylammoniumethyl methacrylate chloride comprising subjecting an aqueous 2-trimethylammoniumethyl methacrylate chloride solution to:

(a) azeotropic removal of water using a $C_{1-6}$ alkyl (meth) acrylate; and (b) filtration of the resulting suspension.

2. The method of claim 1 wherein said $C_{1-6}$ alkyl (meth) acrylate is selected from the group consisting of ethyl acrylate, methyl methacrylate and a mixture thereof.

3. The method of claim 1, wherein said $C_{1-6}$ alkyl (meth)acrylate is methyl methacrylate and is used at a ratio of methyl methacrylate to aqueous 2-trimethylammoniumethyl methacrylate chloride solution in the range of 1:1 to 2:1 by weight.

4. The method of claim 1, further comprising:
a drying a filtrate resulting from process step (b) under mild conditions.

5. The method of claim 4, wherein said drying step is conduced at a temperature $\leq 50°$ C.

6. The method of claim 4, wherein said drying step is conduced at a temperature $\leq 30°$ C.

7. The method of claim 1, wherein said aqueous solution of aqueous 2-trimethylammoniumethyl methacrylate chloride further comprises a polymerization-inhibiting stabilizer.

8. The method of claim 7, wherein said a polymerization-inhibiting stabilizer is 4-hydroxy-2,2,6,6-tetramethylpiperidinyloxy.

9. The method of claim 8, wherein said a polymerization-inhibiting stabilizer is present in an amount of 0.01–0.001 wt. % based on the entire weight of said solution.

10. The method of claim 1, wherein azeotropic removal of water is conducted by the addition of additional air.

11. The method of claim 1, wherein azeotropic removal of water is conducted at a temperature of 40°–90° C.

12. The method of claim 1, wherein said aqueous 2-trimethylammoniumethyl methacrylate chloride solution has a 2-trimethylammoniumethyl methacrylate chloride content of 20–90 wt. % based on the entire weight of said solution.

13. A solid 2-trimethylammoniumethyl methacrylate chloride comprising:
a) 2-trimethylammoniumethyl methacrylate chloride; and
b) 20–50 wt. % based on the total weight of said solid of a $C_{1-6}$ alkyl (meth)acrylate.

14. The solid 2-trimethylammoniumethyl methacrylate chloride of claim 13, which contains $\leq 1$ wt. % of polymeric 2-trimethylammoniumethyl methacrylate chloride.

15. The solid 2-trimethylammoniumethyl methacrylate chloride of claim 13, which is produced by a process comprising:
subjecting an aqueous 2-trimethylammoniumethyl methacrylate chloride solution to:
(a) azeotropic removal of water using a $C_{1-6}$ alkyl (meth)acrylate; and
(b) filtration of the resulting suspension.

16. A polymer obtained by polymerizing:
a solid 2-trimethylammoniumethyl methacrylate chloride comprising:
a) 2-trimethylammoniumethyl methacrylate chloride; and
b) 20–50 wt. % based on the total weight of said solid of a $C_{1-6}$ alkyl (meth)acrylate.

* * * * *